United States Patent [19]
Klein

[11] 4,152,431
[45] May 1, 1979

[54] COMPOSITIONS AND METHOD OF USE
[75] Inventor: Robert W. Klein, Blue Bell, Pa.
[73] Assignee: William H. Rorer, Inc., Fort Washington, Pa.
[21] Appl. No.: 900,805
[22] Filed: Apr. 27, 1978

Related U.S. Application Data

[63] Continuation-in-part of Ser. No. 835,594, Sep. 22, 1977.
[51] Int. Cl.$^2$ ............... A61K 31/44; A61K 31/555
[52] U.S. Cl. .................................. 424/245; 424/263; 424/DIG. 4
[58] Field of Search .................. 424/263, DIG. 4, 245
[56] References Cited

U.S. PATENT DOCUMENTS

| | | | |
|---|---|---|---|
| 3,346,578 | 10/1967 | Langlykke et al. | 424/263 |
| 3,890,434 | 6/1975 | Weisse et al. | 424/DIG. 4 |
| 3,928,605 | 12/1975 | Curry | 424/DIG. 4 |
| 4,049,665 | 9/1977 | Douglas | 424/DIG. 4 |

Primary Examiner—Stanley J. Friedman

[57] ABSTRACT

The present invention relates to a method of topically treating inflammation in warm blooded animals which comprises administering to a warm blooded animal in need of such treatment an effective amount of bis-(2-pyridyl-1-oxide) disulfide and/or the adducts of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2.

11 Claims, No Drawings

COMPOSITIONS AND METHOD OF USE

BACKGROUND OF THE INVENTION

This application is a continuation-in-part of application Ser. No. 835,594, filed Sept. 22, 1977.

The present invention relates to the novel method of treating inflammation in mammals by administering bis-(2-pyridyl-1-oxide) disulfide, the metal salts of bis-(2-pyridyl-1-oxide) disulfide and to novel compositions containing such compounds.

Bis-(2-pyridyl-1-oxide) disulfide (also referred to as 2,2'-dithiodipyridine-1-1'-dioxide) and various derivatives thereof, have previously been disclosed in the literature. For example, U.S. Pat. No. 2,742,476 discloses bis-(2-pyridyl-1-oxide) disulfide and the lower alkyl substituted derivatives thereof. U.S. Pat. No. 3,027,371 discloses molybdate derivatives, U.S. Pat. No. 3,027,732 discloses stannous chloride derivatives, and U.S. Pat. No. 3,346,578 discloses stannous fluoride derivatives of bis-(2-pyridyl-1-oxide) disulfide and each refer to the anti-fungal and antibacterial properties of said derivatives.

U.S. Pat. No. 3,890,434 discloses hair and antiseptic formulations containing adducts of bis-(2-pyridyl-1-oxide) disulfide with alkaline earth metal salts.

DETAILED DESCRIPTION OF THE INVENTION

Now it has been found that bis-(2-pyridyl-1-oxide) disulfide and its adducts having pronounced pharmacological properties for the relief and inhibition of inflammation conditions can be provided according to this invention. More specifically, these adducts have the formula:

$$(C_5H_4NOS)_2MY_t \quad (I)$$

wherein M represents a member selected from the group consisting of zinc, iron, magnesium, tin, cadmium, zirconium, alkali and alkaline earth metals; Y is the anion of an inorganic or organic acid and t is either 1 or 2. More particularly, the anion Y is selected from the group consisting of halides, sulfates, nitrates, chlorates and acetates, with the chlorides and sulfates being most preferable. More particularly preferred are the water soluble adducts especially calcium chloride (CaCl₂) or magnesium sulfate (MgSO₄). Also included in the adducts of this invention are the hydrates of the aforementioned compounds, i.e., adducts including $nH_2O$ groups where n is an integer of 0 to 10. Additionally, the adducts (I) may contain one or more substituents on either or both pyridine ring structures such as alkyls, halogens and alkoxy groups. It is further noted that $(C_5H_4NOS)_2$ as used in (I) above and throughout the specification and claims represents bis-(2-pyridyl-1-oxide) disulfide and the structural formula shown as follows:

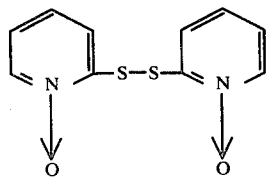

Among the active ingredients which may be utilized in this invention may be mentioned:

Bis-(2-pyridyl-1-oxide)disulfide magnesium sulfate, bis-(2-pyridyl-1-oxide)disulfide magnesium acetate, bis-(2-pyridyl-1-oxide)disulfide magnesium chloride, bis-(2-pyridyl-1-oxide) disulfide magnesium bromide, bis-(2-pyridyl-1-oxide) disulfide calcium chloride, bis-(2-pyridyl-1-oxide)disulfide calcium sulfate, bis-(2-pyridyl-1-oxide) disulfide calcium nitrate, bis-(2-pyridyl-1-oxide) disulfide calcium acetate, bis-(2-pyridyl-1-oxide) disulfide calcium chlorate, bis-(2-pyridyl-1-oxide) disulfide barium chloride, bis-(2-pyridyl-1-oxide) disulfide barium sulfate, bis-(2-pyridyl-1-oxide) disulfide barium nitrate, bis-(2-pyridyl-1-oxide) disulfide barium acetate, bis-(2-pyridyl-1-oxide) disulfide barium chlorate, bis-(2-pyridyl-1-oxide) disulfide strontium chloride, bis-(2-pyridyl-1-oxide) disulfide strontium sulfate, bis-(2-pyridyl-1-oxide)disulfide strontium nitrate, bis-(2-pyridyl-1-oxide) disulfide strontium acetate, bis-(2-pyridyl-1-oxide) disulfide strontium chlorate, bis-(2-pyridyl-1-oxide) disulfide potassium chloride, bis-(2-pyridyl-1-oxide) disulfide potassium sulfate, bis-(2-pyridyl-1-oxide) disulfide potassium nitrate, bis-(2-pyridyl-1-oxide) disulfide potassium acetate, bis-(2-pyridyl-1-oxide) disulfide potassium chlorate, bis-(2-pyridyl-1-oxide) disulfide sodium chloride, bis-(2-pyridyl-1-oxide) disulfide sodium sulfate, bis-(2-pyridyl-1-oxide) disulfide sodium nitrate, bis-(2-pyridyl-1-oxide) disulfide sodium acetate, bis-(2-pyridyl-1-oxide) disulfide sodium chlorate, bis-(2-pyridyl-1-oxide) disulfide zinc chloride, bis-(2-pyridyl-1-oxide) disulfide zinc sulfate, bis-(2-pyridyl-1-oxide) disulfide zinc nitrate, bis-(2-pyridyl-1oxide) disulfide zinc acetate, bis-(2-pyridyl-1-oxide) disulfide zinc chlorate, bis-(2-pyridyl-1-oxide) disulfide stannous chloride, bis-(2-pyridyl-1-oxide) disulfide stannous sulfate, bis-(2-pyridyl-1-oxide) disulfide stannous nitrate, bis-(2-pyridyl-1-oxide) disulfide stannous acetate, bis-(2-pyridyl-1-oxide) disulfide stannous chlorate, bis-(2-pyridyl-1-oxide) disulfide zirconium chloride, bis-(2-pyridyl-1-oxide) disulfide zirconium sulfate, bis-(2-pyridyl-1-oxide) disulfide zirconium nitrate, bis-(2-pyridyl-1-oxide) disulfide zirconium acetate, bis-(2-pyridyl-1-oxide) disulfide zirconium chlorate, bis-(2-pyridyl-1-oxide) disulfide ferrous chloride, bis-(2-pyridyl-1-oxide) disulfide ferrous sulfate, bis-(2-pyridyl-1-oxide) disulfide ferrous nitrate, bis-(2-pyridyl-1-oxide) disulfide ferrous acetate, bis-(2-pyridyl-1-oxide) disulfide ferrous chlorate, bis-(2-pyridyl-1-oxide) disulfide lithium chloride, bis-(2-pyridyl-1-oxide) disulfide lithium sulfate, bis-(2-pyridyl-1-oxide) disulfide lithium nitrate, bis-(2-pyridyl-1-oxide) disulfide lithium acetate, and bis-(2-pyridyl-1-oxide) disulfide lithium chlorate.

In accordance with the present invention, a method of treating inflammation in warm blooded animals is provided which comprises topically administering to a warm blooded animal in need of such treatment an effective amount of bis-(2-pyridyl-1-oxide) disulfide and/or its adducts of Formula I.

As used herein, the term "treatment" is meant to include both active treatment and preventative or prophylactic treatment.

Additionally, bis-(2-pyridyl-1-oxide) disulfide and its adducts (I) utilized in the present invention have been shown to have the property of remaining on the skin and retaining anti-inflammatory activity over a period of time after washing and rinsing of the skin. It is further noted that some of the adducts (I) have the desirable characteristics of being soluble in water and surfactant solutions, thus, they may be used in a wide variety of preparations. More particularly, because of the desirable high solubility of some of the adducts (I) in aqueous solutions, they may be utilized in any clear type formulations.

The present invention also has for its object compositions and means for treating mammals requiring anti-inflammatory treatment including skin conditions such as contact dermatitis, serborrheic dermatitis, atopic dermatitis, neuro dermatitis and the like as well as other mammalian conditions where the symptoms of inflammation and associated pain and fever manifest, such as rheumatic diseases including arthritis tendinitis, erythema, sciatic pain and similar associated veterinary conditions, with from 0.1 to 5% by weight of at least one active compound, preferably from 0.2 to 1.5% by weight. These compositions can be in the form of a solution, a cream, powder, gel, ointment, salve, lotion, or milk. For the treatment of skin conditions the active compounds can also constitute make-up products or dermatological cakes containing the ingredients standard to this type of composition.

Various tests in animals can be carried out to show the ability of the active compounds of this invention to exhibit reactions that can be correlated with anti-inflammatory activity in humans. One such test is the Carrageenan paw edema test, which shows the ability of the instant compounds to inhibit edema induced by injection of an inflammatory agent such as carrageenan into the tissues of the paw of a rat against non-inflamed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone and prednisolone. In view of the results of this test, the active compounds and derivatives can be considered to be active anti-inflammatory agents.

The following examples will further illustrate the formulations containing some of the active compounds of this invention but are not to be considered as limiting the scope of this invention.

EXAMPLE 1

A clear composition having the following formulation was prepared, each of the percentages being based on the total weight of the composition:

| Water | 97.5% |
|---|---|
| $(C_5H_4NOS)_2 \cdot MgSO_4 \cdot 3H_2O$ | 2.5% |
| The pH of this formulation was adjusted to 6.5 | |

Other equally effective and similar compositions are prepared by replacing the magnesium salt in the above formulation with any of the previously mentioned active compounds used in connection with this invention.

EXAMPLE 2

| Bis-(2-pyridyl-1-oxide) disulfide calcium chloride | 2g |
|---|---|
| Titanium oxide | 10g |
| Red iron oxide | 0.3g |
| Yellow iron oxide | 0.2g |
| Brown iron oxide | 0.4g |
| Chestnut iron oxide | 0.2g |

Several stearyl alcohol oxyethylenated with 33 moles of

| Ethylene oxide | 7g |
|---|---|
| Polyglycol stearate | 6g |
| Propyl parahydroxybenzoate | 0.2g |
| Water, Q.S.P. | 100g |

Other creams identical to that described immediately above are prepared by replacing the calcium chloride compound with any of the previously mentioned active compounds.

EXAMPLE 3

A dermatological cake is prepared by mixing together the following components:

| Esters of sodium isothionate and coprafatty acids (sold under the tradename "IGEPON A" having the formula R—COO—CH$_2$—CH$_2$—SO$_3$Na, wherein R equals fatty acid derivatives having 12-15 carbon atoms) | 75 g |
|---|---|
| Lanolin derivatives | 23 g |
| $(C_5H_4NOS)_2 \cdot MgCl_2$ | 2 g |

Other dermatological cakes, identical to the above, are prepared by replacing the magnesium chloride salt of bis-(2-pyridyl-1-oxide) disulfide with any one of the aforementioned active compounds.

EXAMPLE 4

A powder comprising the following mixture:

| Talc | 99g |
|---|---|
| Glycerine oleate | 3g |
| Isopropyl myristate | 7g |
| Bis-(2-pyridyl-1-oxide) disulfide magnesium sulfate | 3g |
| Perfume | 2cc |

Other equally effective powder compositions identical to the above are prepared except that the active ingredient component bis-(2-pyridyl-1-oxide) disulfide magnesium sulfate is replaced by any of the other aforementioned active compounds.

EXAMPLE 5

Cocoa butter (approximately 2.1g) is mixed with bis-(2-pyridyl-1-oxide) disulfide zinc acetate (approximately (0.05g) and the resulting mixture is melted with gentle heat and poured into a mold of a suitable size and shape.

EXAMPLE 6

A tincture is prepared as follows:

| Bis-(2-pyridyl-1-oxide) disulfide barium acetate | 1% |
|---|---|
| Ethanol | 20% |
| Propylene glycol | 10% |
| Water | 69% |

EXAMPLE 7

| Ingredient | |
|---|---|
| Bis-(2-pyridyl-1-oxide) disulfide magnesium chloride | 1% |
| Vitamin E | 2% |
| Propylene glycol | 20% |
| Ethanol | 20% |
| Water | 57% |

EXAMPLE 8

The following ointment base was utilized as a vehicle for the active ingredients of this invention:

| Ingredient | Amount in grams |
|---|---|
| Polyoxyethylene stearyl ether | 5.0 |
| White petrolatum | 5.0 |
| Stearyl alcohol | 15.0 |
| Distilled water | 63.5 |

The ointment containing the above active ingredients were manufactured in the following manner. 3.0 grams bis-(2-pyridyl-1-oxide) disulfide magnesium sulfate were dissolved in a heated mixture of 59 ml of distilled water and 11.50g of propylene glycol. This solution was heated to a temperature of 75° C. and added to a mixture having a like temperature consisting of 15.0g of stearyl alcohol, 5.0g of white petrolatum, 1.0 ml of concentrated ammonia solution and 5.0g of polyoxyethylene stearyl ether, molecular weight about 700. While the resulting mixture was still hot, lactic acid was added to adjust the pH thereof to about 5.5 to approximate the pH of skin. The resulting mixture was thereafter cooled to form a cream which was further worked utilizing a three-roller frame and filled into tubes.

In an analogous manner, ointments were prepared utilizing the following ingredients to form the initial solutions:

a. 2.27 grams bis-(2-pyridyl-1-oxide) disulfide ferrous chloride in 53.23 ml of distilled water and 11.5g of propylene glycol;

b. 2.51 grams of bis-(2-pyridyl-1-oxide) disulfide lithium acetate in 56.19 ml of distilled water and 11.5g of propylene glycol;

c. 2.62 grams of bis-(2-pyridyl-1-oxide) disulfide zirconium chloride in 56.35 ml of distilled water and 11.5g of propylene glycol;

d. 1.0 grams of bis-(2-pyridyl-1-oxide) disulfide strontium chloride in 60.7 ml of distilled water and 11.5g propylene glycol and 0.80 sodium hydroxide. In this example the solution was heated to 75° C. and added to a mixture having a like temperature and containing 1.0 gram of bis-(2-pyridyl-1-oxide) disulfide magnesium sulfate, 13.0 grams of stearyl alcohol, 5.0 grams of polyoxyethylene stearyl ether, molecular weight about 700 and 5.0 grams of white petrolatum, the pH adjusted with lactic acid and the mixture cooled to form a cream which was worked up as above.

EXAMPLE 9

An ointment was prepared by first dissolving 1.5g of bis-(2-pyridyl-1-oxide) disulfide magnesium sulfate and 1.0g of bis-(2-pyridyl-1-oxide) disulfide magnesium chloride in a hot mixture of 57.5g of distilled water and 11.5g of propylene glycol. The resulting solution was heated to 75° C. and added with stirring to a hot (75° C.) mixture of 17.0g of stearyl alcohol, 4.0g of white petroleum jelly and 4.0g of a polyoxyethylene stearyl ether, molecular weight about 700. Lactic acid was added while the emulsion was still hot to adjust the pH thereof to a pH approximating that of skin, i.e., about 5.5. After cooling the resulting cream was further worked utilizing a three-roller frame and filled into tubes.

EXAMPLE 10

An aerosol preparation was formed from the following formulation:

Phase I

| Ingredient | Weight in grams |
|---|---|
| Isopropyl myristate | 18 |
| Stearic acid, cosmetic grade | 30 |
| Myristic acid; cosmetic grade | 9 |
| Glycerin | 18 |

Phase II

| Ingredient | Weight in grams |
|---|---|
| Water | 440 |
| Triethanolamine | 20 |
| Bis-(2-pyridyl-1-oxide) disulfide calcium chloride | 12 |

Phase III

| Ingredient | |
|---|---|
| Panthenol | 6 |
| Suitable perfume | 3 |
| Bis-(2-pyridyl-1-oxide) disulfide magnesium sulfate | 12 |
| Lactic acid q.s. pH | 5.5 |

Phase I and Phase II were separately heated at a temperature of about 75° C. Thereafter, Phase II was added dropwise with vigorous stirring to Phase I which was maintained at a temperature of 75° C. The mixture was then cooled to above 50° C. with stirring and the first three ingredients of Phase III added thereto. The resulting emulsion was mixed and the pH adjusted to about 5.5 with lactic acid. The emulsion was then cooled with stirring to about 20° C.

Nine parts by weight of the emulsion formed above were combined with one part by weight of a propellant (40 dichlorodifluoromethane/60 dichlorotetrafluoroethane) under pressure in suitable aerosol container equipped with conventional valve apparatus and foam-forming head.

EXAMPLE 11

An anti-inflammatory composition in milk form having the following composition:

| Ingredient | Weight in grams |
|---|---|
| Hydrogenated, ethoxylated (10 mol) lanolin | 1.8 |
| Triglyceride of fatty acid of coconut | 7.0 |
| Cetylalcohol | 0.6 |
| Stearylalcohol | 0.6 |
| Paraffin oil (lightweight) | 5.0 |
| Ethylhexyl-p-methoxy cinnamide | 2.5 |
| Stearic acid | 3.0 |
| Bis-(2-pyridyl-1-oxide) disulfide magnesium sulfate | 2.0 |
| Demineralized water | 72.2 |
| Triethanolamine | 0.8 |
| Perfume | 0.5 |

| Ingredient | Weight in grams |
| --- | --- |
| Carboxyvinylpolymer | 2.0 |
| Conservation agent | 2.0 | was manufactured as follows:

A mixture of 1.8g hydrogenated, ethoxylated (10 mol lanolin, 7.0g triglyceride of fatty acid of coconut, 0.6g cetylalcohol, 0.6g stearyl alcohol, 5.0g paraffin oil, 2.5g ethylhexyl-p-methoxy cinnamate and 3.0g of stearic was melted at 70° C. After addition of 2.0g bis-(2-pyridyl-1-oxide) disulfide magnesium sulfate, 2.0g carboxyvinylpolymer in 72.2g demineralized water were added at 70° C. with stirring to the resulting suspension. The mixture was stirred for 15 minutes and then cooled. 0.8g of triethanolamine and 0.5g of perfume were added at 60° C. and 45° C. respectively. The resulting mixture was stirred until cold and a white milk, which was stable at 3,000 Rpm for 1 hour was obtained. Viscosity: 6000 Cp (Brockfield, Spindel, 5, 10 Rpm).

EXAMPLE 11

0.25 g of bis-(2-pyridyl-1-oxide) disulfide is predispersed in 3.0 g of propylene glycol. The mixture is then homogenized into 96.75 grams of finished cream, ointment or lotion following a modification of any one of the procedures of Examples 2, 8, 9 and 11 or as described in F. W. Martin et al, "Remington's Pharmaceutical Sciences", 14th Ed., Mack Publishing Co., Easton, Pa., 1965.

Other agents which have medicinal or therapeutic value may be incorporated in the compositions of this invention.

I claim:

1. A method of treating inflammation in warm blooded animals which comprises topically administering to a warm blooded animal in need of such treatment an effective amount of a compound selected from the group consisting of bis-(2-pyridyl-1-oxide) disulfide and the adducts of bis-(2-pyridyl-1-oxide) disulfide having the empirical formula:

$$(C_5H_4NOS)_2MY_t$$

wherein M represents a member selected from the group consisting of zinc, iron, magnesium, tin, cadmium, zirconium, alkali and alkaline earth metals; Y is the anion of an inorganic or organic acid and t is either 1 or 2.

2. A method of treating inflammation in warm blooded animals which comprises topically administering to a warm blooded animal in need of such treatment an effective amount of a compound selected from the group consisting of bis-(2-pyridyl-1-oxide) disulfide and the adducts of bis-(2-pyridyl-1-oxide) disulfide having the empirical formula:

$$(C_5H_4NOS)_2MY_t$$

wherein M represents a member selected from the group consisting of magnesium, zirconium, alkali and alkaline earth metals; Y is the anion of an inorganic or organic acid and t is either 1 or 2.

3. The method of claim 2, wherein M is magnesium, Y is sulfate and t is 1.

4. The method of claim 2, wherein M is calcium, Y is chloride and t is 2.

5. The method of claim 2, wherein M is calcium, magnesium or barium.

6. The method of claim 2, wherein the compound is selected from the group consisting of $(C_5H_4NOS)_2$, $(C_5H_4NOS)_2 \cdot CaCl_2$, $(C_5H_4NOS)_2MgSO_4 \cdot 3H_2O$, $(C_5H_4NOS)_2SrCl_2$, $(C_5H_4NOS)_2SrBr_2$, $(C_5H_4NOS)_2Ca(NO_3)_2$ and $(C_5H_4NOS)_2Ba(ClO_3)_2$.

7. The method of claim 2, wherein said warm blooded animal is treated for skin conditions requiring anti-inflammatory treatment.

8. The method of claim 7, wherein said skin condition is contact dermatitis, seborrheic dermatitis, atopic dermatitis or neuro dermatitis.

9. The method of claim 2, wherein said adducts are water-soluble.

10. The method of claim 2, wherein Y is selected from the group consisting of halides, sulfates, nitrates and acetates.

11. The method of claim 2, wherein said warm blooded animal is treated for erythema, arthritis, tendinitis or sciatic pain.

* * * * *